United States Patent
Hantash

(10) Patent No.: US 12,415,988 B2
(45) Date of Patent: Sep. 16, 2025

(54) ENHANCED DIFFERENTIATION OF MESENCHYMAL STEM CELLS

(71) Applicant: Escape Therapeutics, Inc., San Jose, CA (US)

(72) Inventor: Basil M. Hantash, East Palo Alto, CA (US)

( * ) Notice: Subject to any disclaimer, the term of this patent is extended or adjusted under 35 U.S.C. 154(b) by 665 days.

(21) Appl. No.: 16/909,616

(22) Filed: Jun. 23, 2020

(65) Prior Publication Data
US 2021/0032599 A1 Feb. 4, 2021

Related U.S. Application Data

(60) Division of application No. 16/040,259, filed on Jul. 19, 2018, now abandoned, which is a continuation of application No. 14/802,857, filed on Jul. 17, 2015, now Pat. No. 10,053,670, which is a continuation of application No. PCT/US2014/012097, filed on Jan. 17, 2014.

(60) Provisional application No. 61/753,993, filed on Jan. 18, 2013.

(51) Int. Cl.
*C12N 5/0775* (2010.01)
*A61K 35/28* (2015.01)

(52) U.S. Cl.
CPC ............ *C12N 5/0662* (2013.01); *A61K 35/28* (2013.01); *C12N 5/0667* (2013.01)

(58) Field of Classification Search
CPC ..... A61K 35/28; C12N 5/0667; C12N 5/0662
See application file for complete search history.

(56) References Cited

U.S. PATENT DOCUMENTS

| | | | |
|---|---|---|---|
| 5,486,359 | A | 1/1996 | Caplan et al. |
| 7,410,773 | B2 | 8/2008 | Abuljadayel |
| 8,647,871 | B2 | 2/2014 | Hantash |
| 2005/0287603 | A1 | 12/2005 | Gorczynski |
| 2008/0213893 | A1 | 9/2008 | Klassen et al. |
| 2010/0055076 | A1 | 3/2010 | Lim et al. |
| 2010/0055785 | A1 | 3/2010 | Hantash |
| 2010/0172885 | A1 | 7/2010 | Pittenger et al. |
| 2011/0256111 | A1 | 10/2011 | Camussi et al. |
| 2011/0262404 | A1 | 10/2011 | Badoer et al. |

FOREIGN PATENT DOCUMENTS

WO WO-2006111706 A1 10/2006

OTHER PUBLICATIONS

Fickert et al. Human mesenchymal stem cell proliferation and osteogenic differentiation during long-term ex vivo cultivation is not age dependent. J Bone Miner Metab (2011) 29:224-235. (Year: 2011).*
Ugurlu et al. Comparison of similar cells: Mesenchymal stromal cells and fibroblasts. Acta Histochemica (2020), 122, 151634, 10 pages. (Year: 2020).*
Mafi et al. Adult Mesenchymal Stem Cells and Cell Surface Characterization—A Systematic Review of the Literature. Open Ortho J (2011), 5, 253-260. (Year: 2011).*
Aggarwal, S. et al., "Human Mesenchymal Stem Cells Modulate Allogeneic Immune Cell Responses", Blood, 105:1815-1822, published online Oct. 19, 2004 (9 pages).
Apps, R. et al., "A critical look at HLA-G", Trends in Immunology, vol. 29, No. 7, pp. 313-321 (2008) (9 pages).
Astarci, E. et al., "The NF-κB Target Genes ICAM-1 and VCAM-1 are Differentially Regulated During Spontaneous Differentiation of Caco-2 Cells", The FEBS Journal, 279:2966-2986, No Month Given, 2012 (21 pages).
Bae, S. et al., "Combined Omics Analysis Identifies Transmembrane 4 L6 Family Member 1 as a Surface Protein Marker Specific to Human Mesenchymal Stem Cells", Stem Cells and Development, 20(2):197-203, published online May 20, 2010 (7 pages).
Bartholomew, A. et al., "Mesenchymal Stem Cells Suppress Lymphocyte Proliferation in Vitro and Prolong Skin Graft Survival in Vitro", Experimental Hematology, 30:42-48, No Month Given, 2002 (7 pages).
Battula, V.L. et al., "Prospective Isolation and Characterization of Mesenchymal Stem Cells from Human Placenta Using a Frizzled-9-Specific Monoclonal Antibody", Differentiation, 76:326-336, No Month Given, 2008 (11 pages).
Beavis, P. et al., "CD73: A Potent Suppressor of Antitumor Immune Responses", Trends in Immunology, 33(5):231-237, May 2012 (7 pages).
Beyth, S et al., "Human Mesenchymal Stem Cells Alter Antigen-Presenting Cell Maturation and Induce T-Cell Unresponsiveness", Blood, 105:2214-2219, published online Oct. 28, 2004 (7 pages).
Blasi, A. et al., "Dermal Fibroblasts Display Similar Phenotypic and Differentiation Capacity to Fat-Derived Mesenchymal Stem Cells, but Differ in Anti-Inflammatory and Angiogenic Potential", Vascular Cell, vol. 3, http://www.vascularcell.com/content/3/1/5, No Month Given, 2011 (14 pages).
Campagnoli, C. et al., "Identification of Mesencymal Stem/Progenitor Cells in Human First-Trimester Fetal Blood, Liver, and Bone Marrow", Blood, 98(8):2396-2402, Oct. 15, 2001 (8 pages).
Colter, D. et al., "Rapid Expansion of Recycling Stem Cells in Cultures of Plastic-Adherent Cells from Human Bone Marrow", PNAS, 97(7):3213-3218, Mar. 28, 2000 (6 pages).
Corcione, A. et al., "Human Mesenchymal Stem Cells Modulate B-Cell Functions", Blood, 107:367-372, published online Sep. 1, 2005 (7 pages).
Covas, D.T., et al., "Multipotent Mesenchymal Stromal Cells Obtained from Diverse Human Tissues share Functional Properties and Gene-Expression Profile with CD146+ Perivascular Cells and Fibroblasts", Experimental Hematology, 36:642-654, 2008 (13 pages).

(Continued)

*Primary Examiner* — Sean C. Barron

(57) ABSTRACT

Isolated populations of mesenchymal stem cells (MSCs) are provided, including mammalian mesenchymal stem cells (MSCs) characterized by the lack of CD54 (CD54$^-$) or low cell-surface CD54 (CD54$^{low}$). Methods of in vitro cell differentiation and methods of treatment using said isolated populations are also provided.

14 Claims, 7 Drawing Sheets

Specification includes a Sequence Listing.

(56) References Cited

OTHER PUBLICATIONS

Dicker, A. et al., "Functional Studies of Mesenchymal Stem Cells Derived from Adult Human Adipose Tissue", Experimental Cell Research, vol. 308, No. 2, pp. 283-290, Aug. 15, 2005 (9 pages).
Dominici, M. et al., "Minimal Criteria for Defining Multipotent Mesenchymal Stromal Cells, The International Society for Cellular Therapy Position Statement", Cytotherapy, vol. 8, No. 4, pp. 315-317, 2006 (3 pages).
Friedenstein, A. et al., "Stromal Cells Responsible for Transferring the Microenvironment of the Hemopoietic Tissues", Transplantation, 17(4):331-340, Apr. 1974 (10 pages).
Golde, D.W. et al., "Origin of Human Bone Marrow Fibroblasts", British Journal of Haematology, 44:183-187, No Month Given, 1980 (5 pages).
Goncalves, Manuel A.F.V., et al., "Human mesenchymal stem cells ectopically expressing full-lenth dystrophin can complement Duchenne muscular dystrophy myotubes by cell fusion," Human Molecular Genetics, vol. 15, No., 2, pp. 213-221 (2006) (9 total pages).
Gonsalves, M., et al., "Transduction of Myogenic Cells by Retargeted Dual High-Capacity Hybrid Viral Vectors: Robust Dystrophin Synthesis in Duchenne Muscular Dystrophy Muscle Cells", Molecular Therapy, 13(5): 976-986, May 2006 (11 pages).
Gotherstrom, C. et al., "Difference in Gene Expression Between Human Fetal Liver and Adult Bone Marrow Mesenchymal Stem Cells", Haematologica/The Hematology Journal, 90(8):1017-1026, 2005 (10 pages).
Gronthos, S. et al., "Surface Protein Characterization of Human Adipose Tissue-Derived Stromal Cells", Journal of Cellular Physiology, vol. 189, pp. 54-63, May 25, 2011 (10 pages).
Haniffa, M. et al., "Mesenchymal Stem Cells: The Fibroblasts' New Clothes?", haematologica 94(2):258-263, No Month Given, 2009 (6 pages).
Hee, C. et al., "Influence of Three-Dimensional Scaffold on the Expression of Osteogenic Differentiation Markers by Human Dermal Fibroblasts", Biomaterials, 27:875-884. available online Aug. 15, 2005 (10 pages).
Horwitz, EM et al., "Clarification of the Nomenclature for MSC: The International Society for Cellular Therapy Position Statement", Cytotherapy, 7(5):393-395, No Month Given, 2005 (4 pages).
International Search Report and Written Opinion issued by the European Patent Office as Searching Authority in PCT/US2008/058779, mailed Mar. 10, 2009 (14 pages).
International Search Report and Written Opinion issued by the U.S. Patent and Trademark Office as International Searching Authority, for International Application No. PCT/US14/12097, dated May 12, 2014 (11 pages).
Iwashima, S. et al., "Novel Culture System of Mesenchymal Stromal Cells from Human Subcutaneous Adipose Tissue", Stem Cells and Development, 18(4):533-543, available online Dec. 4, 2008 (12 pages).
Izadpanah, et al. "Long-term In vitro Expansion Alters the Biology of Adult Mesenchymal Stem Cells", Cancer Res. 68(11):4229-4238, 2008.
Jiang, X. et al., "Human Mesenchymal Stem Cells Inhibit Differentiation and Function of Monocyte-Derived Dendritic Cells", Blood, 105:4120-4126, published online Feb. 3, 2005 (8 pages).
Junker, J. et al., "Adipogenic, Chondrogenic and Osteogenic Differentiation of Clonally Derived Human Dermal Fibroblasts", Cells Tissues Organs, 191:105-118, published online Jul. 28, 2009 (14 pages).
Kawabata, K. et al., "Adenovirus Vector-Mediated Gene Transfer Into Stem Cells", Molecular Pharmaceutics, American Chemical Society. vol. 3, No. 2, Jan. 21, 2006, pp. 95-103 (9 pages).
Kolios, G., et al., "Introduction to Stem Cells and Regeneratie Medicine", Thematic Review Series 2013, Respiration, 85:3-10, available online Dec. 13, 2012 (8 pages).
Lai, R. et al., "Exosome Secreted by MSC Reduces Myocardial Ischemia/Reperfusion Injury", Stem Cell Research 4(3):214-222, May 2010 (9 pages).

Le Blanc, K. et al., "HLA Expression and Immunologic Properties of Differentiated and Undifferentiated Mesenchymal Stem Cells", Experimental Hematology, NY, NY, US, vol. 31, No. 10, Oct. 1, 2003, pp. 890-896 (7 pages).
Lee, Ryang Hwa et al., "Characterization and Expression Analysis of Mesenchymal Stem Cells from Human Bone Marrow and Adipose Tissue", Cellular Physiology and Biochemistry, vol. 14, pp. 311-324, 2004 (14 pages).
Lorenz, K, et al., "Multilineage Differentiation Potential of Human Dermal Skin-Derived Fibroblasts", Experimental Dermatology, 17:925-932, No Month Given, 2008 (8 pages).
Meisel, R. et al., "Human Bone Marrow Stromal Cells Inhibit Allogeneic T-Cell Responses by Indoleamine 2,3-dioxygenase—Mediated Tryptophan Degradation", Blood, 103:4619-4621, published online Mar. 4, 2004 (4 pages).
Miyazaki, et al., "Isolation of two human fibroblastic cell populations with multiple but distinct potential of mesenchymal differentiation by ceiling culture of mature fat cells from subcutaneous adipose tissue", Differentiation, 73:69-78 (2005).
Nasef, A. et al., "Immunosuppressive Effects of Mesenchymal Stem Cells: Involvement of HLA-G", Transplantation, vol. 84, No. 2, pp. 231-237, Jul. 27, 2007 (7 pages).
Nasef, A. et al., "Inhibition of T Lymphocyte (TL) Proliferation by Mesenchymal Stem Cells (MSCs): Role of Cell Contact Between MSCs and TL, Role of MSCs Dose Effect, and Role of Soluble Factors and Adhesion Molecules Exprssed by MSCs", Blood, ASH Annual Meeting Abstract. vol. 104, Abstract 4251, No Month Listed 2004, (1 page).
Nauta, A. et al., "Mesenchymal Stem Cells Inhibit Generation and Function of Both $CD34^{+}$—Derived and Monocyte-Derived Dendritic Cells", Journal of Immunology, 177(4):2080-2087, Aug. 15, 2006 (9 pages).
Niarchos, D. et al., "Characterization of a Novel Cell Penetrating Peptide Derived from Bag-1 Protein", Peptides, 27:2661-2669, published online Jun. 30, 2006 (9 pages).
No Author Listed, "Symposium I—HLA-G: Structure and Function", Abstracts from the 4th International Conference on HLA-G, Museum National d'Histoire Naturelle, Paris, France, Jul. 10-12, 2006, Tissue Antigens. vol. 68, pp. 349-368 (20 pages).
Oedayrajsingh-Varma, MJ et al., "Adipose Tissue-Derived Mesenchymal Stem Cell Yield and Growth Characteristics are Affected by the Tissue-Harvesting Procedure", Cytotherapy, vol. 8, No. 2, pp. 166-177, 2006 (12 pages).
Pilling, D. et al., "Identification of Markers that Distinguish Monocyte-Derived Fibrocytes from Monocytes, Macrophages, and Fibroblasts", PLOS One, 4(10): e7475, published Oct. 16, 2009 (18 pages).
Prockop, D. et al., "Clinical Trials with Adult Stem/Progenitor Cells for Tissue Repair: Let's Not Overlook Some Essential Precautions", Blood, 109:3147-3151, published online Dec. 14, 2006 (6 pages).
Rajagopalan, S. et al., "Activation of NK Cells by an Endocytosed Receptor for Soluble HLA-G", PL°S Biology, Jan. 2006, vol. 4, Issue 1, e9, pp. 0070-0086 (17 pages).
Reddy, B. et al., "Mesenchymal Stem Cells as Immunomodulator Therapies for Immune-Mediated Systemic Dermatoses", Stem Cells and Development, 21(3):352-362, published online Aug. 24, 2011 (11 pages).
Romanov, Yu A. et al., "Mesenchymal Stem Cells from Human Bone Marrow and Adipose Tissue: Isolation, Characterization and Differentiation Potentialities", Cell Technologies in Biology and Medicine, Springer Science + Business Media, Inc., No. 3. Sep. 2005, pp. 138-143 (6 pages).
Ryan, J. et al., "Mesenchymal Stem Cells Avoid Allogeneic Rejection", Journal of Inflammation, vol. 2, No. 8, http://www.journal-inflammation.com/content/2/1/8, published Jul. 26, 2005 (11 pages—entire document).
Sasaki, H. et al., "HLA-E and HLA-G Expression on Porcine Endothelial Cells Inhibit Xenoreactive Human NK Cells Through CD94/NKG2-Dependent and -Independent Pathways", The Journal of Immunology, vol. 163, 1999, pp. 6301-6305 (5 pages).

(56) References Cited

OTHER PUBLICATIONS

Schäffler, Andreas et al., "Concise Review: Adipose Tissue-Derived Stromal Cells—Basic and Clinical Implications for Novel Cell-based Therapies", Stem Cells, vol. 25, pp. 818-827, Dec. 1, 2006 (10 pages).

Sengenès, Coralie et al., "Preadipocytes in the Human Subcutaneous Adipose Tissue Display Distinct Features from the Adult Mesenchymal and Hematopoietic Stem Cells", Journal of Cellular Physiology, vol. 205, No. 1, pp. 114-122, Oct. 2005 (10 pages).

Shang, X. et al., "Contribution of CD11a/CD18, CD11b/CD18, ICAM-1 (CD54) and -2 (CD102) to Human Monocyte Migration through Endothelium and Connective Tissue Fibroblast Barriers", Eur. J. Immunol., 28:1970-1979, No Month Given, 1998 (10 pages).

Sommar, P. et al., "Engineering Three-Dimensional Cartilage- and Bone-like Tissues using Human Dermal Fibroblasts and Macroporous Gelatine Microcarriers", Journal of Plastic, Reconstructive & Aesthetic Surgery, 63:1036-1046, No Month Given, 2010 (11 pages).

Spaggiari, G. et al., "Mesenchymal Stem Cells Inhibit natural Killer-Cell Proliferation, Cytotoxicity, and Cytokine Production: Role of Idoleamine 2,3-dioxygenase and Prostaglandin E2", Blood, 111:1327-1333, published online Oct. 19, 2007 (8 pages).

Uccelli, A. et al., "Mesenchymal Stem Cells in Health and Disease", Nature, 8:726-736, published online Aug. 18, 2008 (12 pages).

Villaron, E. et al., "Mesenchymal Stem Cells are Present in Peripheral Blood and can Engraft After Allogeneic Hematopoietic Stem Cell Transplantation", Hematopoietic Stem Cells, 89(12):1421-1427, Dec. 2004 (7 pages).

Wagner, W. et al., "Comparative Characteristics of Mesenchymal Stem Cells from Human Bone Marrow, Adipose Tissue, and Umbilical Cord Blood", Experimental Hematology, 33:1402-1416, No Month Given, 2005 (15 pages).

Wang, et al., "Support of Human Adipose-Derived Mesenchymal Stem Cell Multipotency by a Poloxamer-Octapeptide Hybrid Hydrogel", Biomaterials, 31:5122-5130, published online Mar. 26, 2010 (9 pages).

Yang, L. et al., "ICAM-1 Regulates Neutrophil Adhesion and Transcellular Migration of TNF-α-activated Vascular Endothelium Under Flow", Blood, 106:584-592, published online Apr. 5, 2005 (10 pages).

Yelavathi, Krishna K. et al., "Analysis of HLA-G mRNA in Human Placental and Extraplacental Membrane Cells by in Situ Hybridization", The Journal of Immunology, vol. 146, No. 8, pp. 2847-2854, Apr. 15, 1991, (8 pages).

Zeddou, M. et al., "The Umbilical Cord Matrix is a Better Source of Mesenchymal Stem Cells (MSC) than the Umbilical Cord Blood", Cell Biology International, 34(7):693-701, published Mar. 1, 2010 (9 pages).

Zhang, B., "CD73: A Novel Target for Cancer Immunotherapy", Cancer Research, 70(16):6407-6411, published online Aug. 3, 2010 (6 pages).

Zhao, L. et al., "Novel Negative Selection Marker CD54 Enhances Differentiation of Human Adipose-Derived Mesenchymal Stem Cells", J. Clin. Cell Immunol S9:005. doi:10.4172/2155-9899.S9-005, No Month Given 2013 (6 pages).

Zuk, P. et al., "Multilineage Cells from Human Adipose Tissue: Implications for Cell-Based Therapies", Tissue Engineering, 7(2):211-228, No Month Given, 2001 (18 pages).

Alegre-Aguaron et al., "Differences in Surface Marker Expression and Chondrogenic Potential among Various Tissue-Derived Mesenchymal Cells from Elderly Patients with Osteoarthritis," Cells Tissues Organs, Mar. 20, 2012, vol. 196, pp. 231-240.

Alt et al., "Fibroblasts share mesenchymal phenotypes with stem cells, but lack their differentiation and colony-forming potential," Biology of the Cell, Feb. 18, 2011, vol. 103(4), pp. 197-208.

Dhanasekaran et al., "Surface antigenic profiling of stem cells from human omentum fat in comparison with subcutaneous fat and bone marrow," Cytotechnology, Feb. 1, 2012, vol. 64, pp. 497-509.

Halfon et al., "Markers distinguishing mesenchymal stem cells from fibroblasts are downregulated with passaging," Stem Cells and Development (2011), published online Jun. 7, 2010, vol. 20(1), pp. 53-66.

Hashikawa et al., "Involvement of CD73 (ecto-5'-nucleotidase) in Adenosine Generation by Human Gingival Fibroblasts," J. Dent. Res., Nov. 2003, vol. 82(11), pp. 888-892.

Karlsson et al., "Stromal cells from term fetal membrane are highly suppressive in allogeneic settings in vitro," Clinical and Experimental Immunology, Mar. 2012, vol. 167, pp. 543-555.

Lange et al., "Marrow Cells Cultured in MSC Medium Expand to CD73, CD90 and CD105 Cells of Fibroblast-Like Morphology," Nov. 16, 2005, vol. 106(11):4319. 2 pages.

Qiao et al., "[Effects of interferon-γ on expression of adhesion molecules in human umbilical cord mesenchymal stromal cells]," Zhongguo Shi Yan Xue Ye Xue Za Zhi. Oct. 2012;20(5):1195-9. Chinese. PMID: 23114147. Abstract, PubMed, NIH National Library of Medicine, 1 page.

Rong et al., "[Effects of interferon-γ on biological characteristics and immunomodulatory property of human umbilical cord-derived mesenchymal stem cells]," Zhongguo Shi Yan Xue Ye Xue Za Zhi. Apr. 2012;20(2):421-6. Chinese. PMID: 22541112. Abstract, PubMed, NIH National Library of Medicine, 1 page.

Sudo et al., "Mesenchymal progenitors able to differentiate into osteogenic, chondrogenic, and/or adipogenic cells in vitro are present in most primary fibroblast-like cell populations," Stem Cells, Jul. 2007, vol. 25, pp. 1610-1617.

* cited by examiner

ENHANCED DIFFERENTIATION OF MESENCHYMAL STEM CELLS

CROSS-REFERENCE TO RELATED APPLICATIONS

This application is a divisional of U.S. patent application Ser. No. 16/040,259 filed on Jul. 19, 2018, which is a continuation of U.S. patent application Ser. No. 14/802,857 filed on Jul. 17, 2015, which is a continuation of International Patent Application No. PCT/US2014/012097 filed on Jan. 17, 2014, which claims the benefit of and priority to U.S. Provisional Application No. 61/753,993 filed on Jan. 18, 2013. All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

FIELD OF THE INVENTION

This invention generally relates to mesenchymal stem cells, and compositions and methods thereof. U.S. application Ser. No. 12/532,512, filed Sep. 22, 2009, also generally relates to mesenchymal stem cells, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 28, 2020, is named 2200876-00127US4_SL.txt and is 4,918 bytes in size.

BACKGROUND OF THE INVENTION

Mesenchymal stem cells (MSCs) are self-renewing multipotent cells capable of differentiating into several cell lineages including osteoblasts, chondrocytes, and adipocytes. Ryan, J. M. et al. *Mesenchymal stem cells avoid allogenic rejection*, J Inflamm (Lond), 2005. 2: p. 8. First described by Friedenstein et al. (Friedenstein, A. J., et al., *Stromal cells responsible for transferring the microenvironment of the hemopoietic tissues. Cloning in vitro and retransplantation in vivo*, Transplantation, 1974. 17(4): p. 331-40), MSCs have successfully been isolated from bone marrow (Friedenstein, A. J., et al.; Golde, D. W., et al., *Origin of human bone marrow fibroblasts*, Br J Haematol, 1980. 44(2): p. 183-7), adipose (Zuk, P. A., et al., *Multilineage cells from human adipose tissue: implications for cell-based therapies*, Tissue Eng, 2001. 7(2): p. 211-28.; Iwashima, S., et al., *Novel culture system of mesenchymal stromal cells from human subcutaneous adipose tissue*, Stem Cells Dev, 2009. 18(4): p. 533-43), peripheral blood (Wagner, W., et al., *Comparative characteristics of mesenchymal stem cells from human bone marrow, adipose tissue, and umbilical cord blood*, Exp Hematol, 2005. 33(11): p. 1402-16), umbilical cord blood and matrix (Zeddou, M., et al., *The umbilical cord matrix is a better source of mesenchymal stem cells (MSC) than the umbilical cord blood*, Cell Biol Int.), fetal blood and liver (Campagnoli, C., et al., *Identification of mesenchymal stem/progenitor cells in human first-trimester fetal blood, liver, and bone marrow*, Blood, 2001. 98(8): p. 2396-402), connective tissue of dermis (Wagner, W., et al.; Lorenz, K., et al., *Multilineage differentiation potential of human dermal skin-derived fibroblasts*, Exp Dermatol, 2008 17(11): p. 925-32), and skeletal muscle sources (Wagner, W., et al.). The multi-differentiation potential of MSC raises a clinical interest to employ these cells for regeneration purposes, for example, in osteogenesis imperfecta. MSCs lack major histocompatibility complex class II antigens and have been shown in vitro to inhibit the activation and/or function of natural killer cells (Spaggiari, G. M., et al., *Mesenchymal stem cells inhibit natural killer-cell proliferation, cytotoxicity, and cytokine production: role of indoleamine 2,3-dioxygenase and prostaglandin E2*, Blood, 2008. 111(3): p. 1327-33), T cells (Meisel, R., et al., *Human bone marrow stromal cells inhibit allogeneic T-cell responses by indoleamine 2, 3-dioxygenase-mediated tryptophan degradation*, Blood, 2004. 103(12): p. 4619-21; Aggarwal, S. and M. F. Pittenger, *Human mesenchymal stem cells modulate allogeneic immune cell responses*, Blood, 2005. 105(4): p. 1815-22; Bartholomew, A., et al., *Mesenchymal stem cells suppress lymphocyte proliferation in vitro and prolong skin graft survival in vivo*, Exp Hematol, 2002. 30(1): p. 42-8), dendritic cells (Beyth, S., et al., *Human mesenchymal stem cells alter antigen-presenting cell maturation and induce T-cell unresponsiveness*, Blood, 2005. 105(5): p. 2214-9; Jiang, X. X., et al., *Human mesenchymal stem cells inhibit differentiation and function of monocyte-derived dendritic cells*, Blood, 2005. 105(10): p. 4120-6; Nauta, A. J., et al., *Mesenchymal stem cells inhibit generation and function of both CD34+-derived and monocyte-derived dendritic cells*, J Immunol, 2006. 177(4): p. 2080-7), and B-cells (Corcione, A., et al., *Human mesenchymal stem cells modulate B-cell functions*, Blood, 2006. 107(1): p. 367-72). These immunomodulatory properties have led to clinical trials to assess their therapeutic potential for graft-versus-host disease after hematopoietic transplantation, type I diabetes, and multiple sclerosis. Due to easy access via liposuction, adipose has become the preferred source of MSCs for therapeutic applications.

Irrespective of their source, MSC isolation involves several steps including positive selection via the properties of plastic-adherence and colony formation (Uccelli, A., L. Moretta, and V. Pistoia, *Mesenchymal stem cells in health and disease*, Nat Rev Immunol, 2008. 8(9): p. 726-36). Although this eliminates contaminants such as blood and immune cells, a heterogeneous starting population and fibroblast contamination represent disadvantages. Fibroblasts are known to undergo senescence and apoptosis in culture, while surviving cells become immortal and potentially tumorogenic. Prockop, D. J. and S. D. Olson, *Clinical trials with adult stem/progenitor cells for tissue repair: let's not overlook some essential precautions*, Blood, 2007. 109(8): p. 3147-51. Thus, identification and elimination of fibroblasts from MSC culture could improve MSC yield and differentiation potential and also prevent tumor formation after MSC transplantation.

However, there are currently no markers which can be used to identify and isolate MSCs. Despite consensus that MSCs are positive for expression of CD73, CD90, and CD105, and negative for expression of hematopoietic cell surface markers CD11a, CD19, CD34, CD45, and HLA-DR (Horwitz, E. M., et al., *Clarification of the nomenclature for MSC: The International Society for Cellular Therapy position statement*, Cytotherapy, 2005. 7(5): p. 393-5), expression levels of these markers vary across laboratories due to tissue source or the specific culture conditions used. Uccelli, et al. Perhaps more importantly, fibroblasts also express CD105, CD73, and CD90 on their surface and lack hematopoietic markers. Covas, D. T., et al., *Multipotent mesenchymal stromal cells obtained from diverse human tissues share functional properties and gene-expression profile with CD146+perivascular cells and fibroblasts*, Exp Hematol, 2008. 36(5): p. 642-54. Additionally, fibroblasts and MSCs share an almost identical in vitro morphology, rendering useless physical filtration techniques. Haniffa, M. A., et al., *Mesenchymal stem cells: the fibroblasts' new clothes?* Haematologica, 2009. 94(2): p. 258-63.

SUMMARY OF THE INVENTION

Due to their multi-differentiation potential and immunosuppressive function, mesenchymal stem cells (MSCs) hold great promise in regenerative medicine. Lack of specific selection markers to isolate MSCs renders their use at risk of fibroblast contamination. Thus, more effective strategies to purify MSCs are needed.

One object of the invention is to provide new cell-surface protein markers that can be used for MSC purification during in vitro expansion. For example, adipose-derived MSCs (AMSCs) and dermal fibroblasts were compared using real-time RT-PCR and flow cytometry and CD54 was identified as a novel negative selection marker that enhances MSC differentiation potential. With real-time RT-PCR, it was demonstrated that primary human dermal fibroblasts expressed CD54 mRNA 10-fold more than early passage human adipose-derived MSCs (AMSCs). Flow cytometry illustrated 88.0%±4.1% of dermal fibroblasts strongly expressed CD54 on their surface with a mean fluorescence intensity ratio of 24.0±0.0 compared to 11.0%±0.7% and minimal intensity for AMSCs. Evaluation of CD54 sorted AMSCs revealed CD73 expression was 2.2-fold higher in the CD54$^-$ versus CD54$^+$ fraction. CD54$^-$ AMSCs demonstrated increased adipogenic and osteogenic differentiation potential relative to CD54$^+$ AMSCs. Accordingly, CD54 (also known as ICAM1, or intercellular adhesion molecule 1) is a novel selection marker capable of distinguishing MSCs from fibroblasts and thus enhances MSC osteogenic and adipogenic differentiation potential.

In one aspect, the invention provides a method for enhancing MSC differentiation potential comprising: (1) isolating a population of MSCs that have low or no cell-surface expression of CD54, and (2) differentiating said CD54$^{low}$ or CD54$^-$ MSCs such that the percentage of cells differentiated is greater than the percentage of differentiated cells from CD54$^+$ MSCs or from a population of MSCs that are unsorted/non-isolated on the basis of CD54 cell-surface expression.

As used herein, MSCs can be considered to have "low" cell-surface CD54 expression when the mean fluorescence intensity (MFI) level or median fluorescence intensity level of CD54 relative to an isotype-matched negative control is less than 5, 4, 3, 2, or 1. The mean or median fluorescence intensity level can be measured, for example, by flow cytometry. In flow cytometry, for example, a fluorophore labeled antibody specific to CD54 is used to determine the cell-surface expression level of CD54. An isotype-matched negative control antibody is an antibody that is not specific to CD54, but has the same isotype, i.e., IgG subclass, IgM, IgD, IgE, etc., as the anti-CD54 labeled antibody.

As used herein, enhanced MSC differentiation refers to comparing the percentage of MSCs that differentiate under standard conditions into different cell-type lineages, such as osteoblasts, chondrocytes, or adipocytes. Other non-limiting examples of mesenchymal derived tissues include fibroblasts, neurons, endothelial cells, myoblasts, and any other MSC-derived cells including corneal stroma and dental pulp of deciduous baby teeth. In a general sense, differentiation of parent MSC cell to progeny cells refers to the loss of some degree of multipotency of the differentiated progeny cells as compared to the parent MSC. MSC differentiation is enhanced if the percentage of differentiated cells is increased when using with CD54$^{low}$ or CD54$^-$ MSCs as compared to CD54$^+$ MSCs or MSCs that are unsorted or unseparated on the basis of cell-surface CD54 expression. In certain embodiments, MSC differentiation is enhanced if the CD54$^{low}$ or CD54$^-$ MSCs provide a greater percentage of differentiated cells, such as about a 1.5-fold, 2-fold, 3-fold, 4-fold, or 5-fold greater percentage, as compared to the percentage of differentiated cells from CD54$^+$ MSCs or MSCs that are unsorted or unseparated on the basis of cell-surface CD54 expression.

As used herein, an MSC can be any mesenchymal stem cell, including MSCs isolated or derived from bone marrow (Friedenstein, A. J., et al.), adipose (Zuk, P. A., et al.; Iwashima, S., et al.), peripheral blood (Wagner, W., et al.), umbilical cord blood and matrix (Zeddou, M., et al.), and liver (Campagnoli, C., et al.), connective tissue of dermis (Wagner, W., et al.; Lorenz, K., et al.), and skeletal muscle sources (Wagner, W., et al.). The MSCs can be any mammalian cell, including rodent, bovine, equine, and primate cells. In a preferred embodiment, the MSCs are human MSCs. Human MSCs have been previously characterized to express a number of cell-surface proteins, including CD54, CD9, CD29, CD44, CD56, CD61, CD63, CD71, CD73, CD90, CD97, CD98, CD99, CD105, CD106, CD112, CD146, CD155, CD166, CD276, and CD304. Human MSCs are often characterized by the cell-surface expression of CD29, CD44, CD73, CD90, and CD105, (with a consensus of CD73, CD90, and CD105), the absence of cell-surface expression of hematopoietic markers such as CD11a, CD19, CD34, CD45, and the absence of HLA-DR. Horwitz, E. M., et al.

In another aspect, the invention provides an isolated population of MSCs where the population is characterized by low or no cell-surface CD54 expression. In certain embodiments, the isolated population comprises, for example, greater than 50%, 60%, 70%, 75%, 80%, 85%, 90%, 95%, 96%, 97%, 98%, or 99% of CD54$^{low}$ or CD54$^-$ MSCs.

In one embodiment, the isolated population of MSCs is characterized by having a cell-surface marker expression profile comprising: CD54$^{low}$ or CD54$^-$, CD73$^+$, CD90$^+$, CD105$^+$, CD11a$^-$, CD19$^-$, and CD34$^-$.

In one embodiment, the isolated population of MSCs is characterized by having a cell-surface marker expression profile comprising: CD54$^{low}$ or CD54$^-$, CD29$^+$, CD44$^+$, CD73$^+$, CD90$^+$, CD105$^+$, CD34$^-$, and CD45$^-$.

In one embodiment, the CD54$^{low}$ or CD54$^-$ MSCs further express endogenous HLA-G (HLA-G$^+$ MSC), HLAE (HLA-E$^+$ MSC), or HLA-G and HLA-E (HLA-G$^+$/HLA-E$^+$ MSC); wherein such expression may be intracellular, as a cell surface marker(s), and/or as soluble protein. In one embodiment, the isolated MSC population has a cell-surface expression profile comprising CD54$^{low}$ or CD54$^-$ and HLA-G$^+$. In one embodiment, the CD54$^{low}$ or CD54$^-$ MSCs further express indoleamine-pyrrole 2,3, dioxygenase (INDO). In one embodiment, the CD54$^{low}$ or CD54$^-$ MSCs further express CD200. Other examples of MSC cell surface markers may be found in U.S. application Ser. No. 12/532,512, filed Sep. 22, 2009, the content of which is hereby incorporated by reference in its entirety.

In one embodiment, the invention provides for methods and compositions relating to isolated populations of MSCs that are CD54$^{low}$ or CD54$^-$ and are substantially free of fibroblasts. As used herein, substantially free of fibroblasts can be a population of CD54$^{low}$ or CD54$^-$ MSCs that comprise less than 5%, 4%, 3%, 2%, 1%, 0.5%, or 0.1% of contaminating fibroblasts.

In one embodiment, the invention provides an isolated population of MSCs that comprises CD54$^{low}$ or CD54$^-$ and cell-surface CD73 expression that is at least 1.5 or 2-fold higher relative to CD54$^+$ MSCs. Such a CD54$^{low}$ or CD54$^-$ MSC subpopulation that expresses greater amounts of cell-surface CD73 as compared to CD54$^+$ MSCs is useful for immunosuppression applications. CD73, a membrane-bound nucleotidase, is pivotal in the conversion of immunostimulatory ATP into adenosine, which exerts potent immunosuppressive effects on both CD4$^+$ and CD8$^+$ T cells. Beavis, P. A., et al., *CD73: a potent suppressor of antitumor immune responses*, Trends Immunol, 2012. 33(5): p. 231-7; Zhang, B., *CD73: a novel target for cancer immunotherapy*, Cancer Res, 2010. 70(16): p. 6407-11. Thus, increased CD73 expression in CD54$^-$ MSCs would benefit their immunosuppressive effects. Accordingly, methods of immunosuppression are also provided by the invention, where the method comprises administering to a subject allogeneic CD54$^{low}$ or CD54$^-$ MSCs. For the purposes of this invention, the cells may be allogeneic, autologous, or xenogeneic with respect to the recipient. For example, the CD54$^{low}$ or CD54$^-$ MSCs do not require a perfect match of histocompatibility antigens relative to the subject. In one embodiment, the immunosuppression method comprises administering to a subject allogeneic CD54$^{low}$ or CD54$^-$ MSCs that express cell-surface CD73 at least 1.3-fold, 1.5-fold, 1.75-fold, or 2-fold greater than allogeneic CD54$^+$ MSCs. In one embodiment, the subject is suffering from one or more conditions selected from type 1 diabetes, graft-versus-host disease, autoimmune disease, inflammatory bowel disease, and cardiac disease. In one embodiment, the subject is suffering from a condition selected from the group consisting of graft-versus-host disease, type I diabetes, sclerosis, and lupus. In one embodiment, the subject is suffering from a condition selected from the group consisting of graft-versus-host disease after hematopoietic transplantation, type I diabetes, and multiple sclerosis. In one embodiment, the allogeneic CD54$^{low}$ or CD54$^-$ MSCs are administered in an amount sufficient to suppress the activation of CD4$^+$ or CD8$^+$ T-cells against transplantation, in type I diabetes, or in autoimmune disease.

In some embodiments, the CD54$^{low}$ or CD54$^-$ MSCs described herein are immunosuppressive against the activation and/or function of natural killer cells, neutrophils, T cells, dendritic cells, and/or B-cells. These immunomodulatory properties of the CD54$^{low}$ or CD54$^-$ MSCs described herein may be used as therapeutic treatment for graft-versus-host disease after hematopoietic transplantation, type I diabetes, and multiple sclerosis. In one embodiment, CD54$^{low}$ or CD54$^-$ MSCs described herein may be used in the induction and maintenance of immune system regulation in post-infectious, inflammatory, allergic, autoimmune, alloimmune, vasculitic, degenerative vascular, and graft-versus-host diseases.

BRIEF DESCRIPTION OF THE FIGURES

A more complete appreciation of the present invention and many of its advantages will be understood by reference to the following detailed description when considered in connection with the following drawings, which are presented for the purpose of illustration only and are not intended to be limiting, and in which.

DETAILED DESCRIPTION

Figure 1:
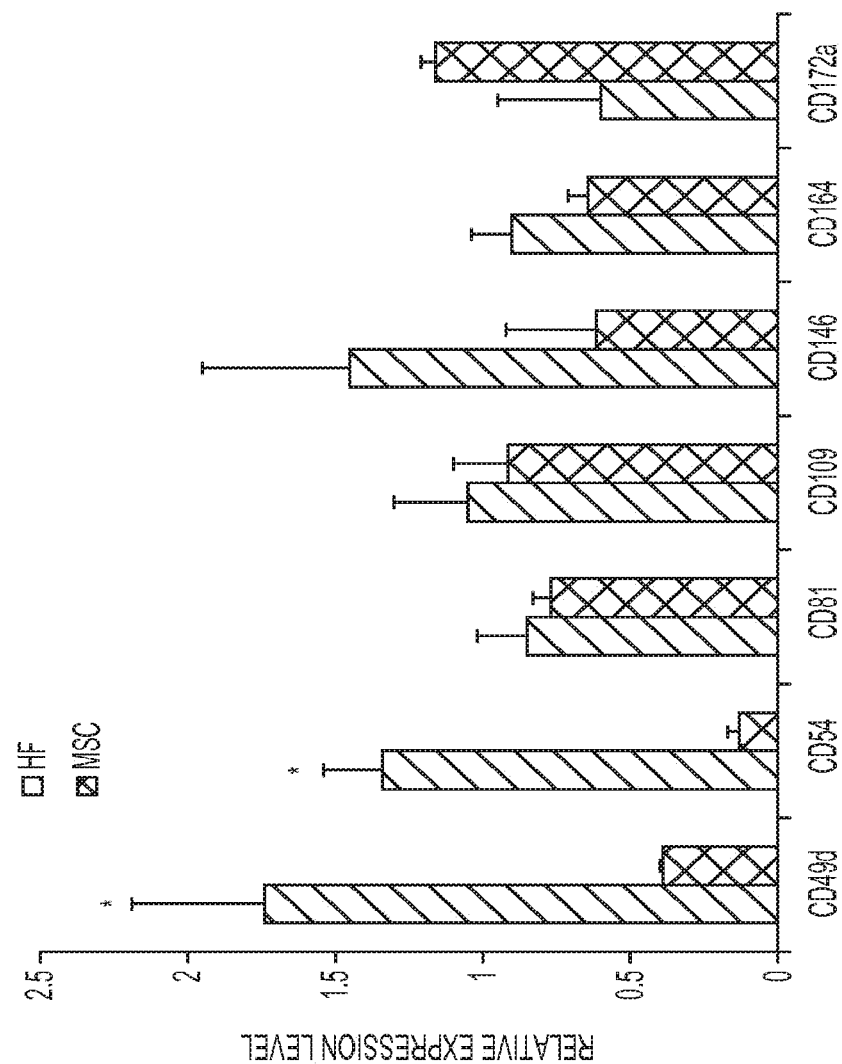
FIG. 1. Expression profile of CD markers on AMSCs and fibroblasts. Cells were taken from early (≤5) cell culture passages.

The following explanations of terms and examples are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

MSCs can be obtained, for example, from bone marrow or adipose tissue. As stated above, human MSCs have been previously characterized to express a number of cell-surface proteins, including CD54, CD9, CD29, CD44, CD56, CD61, CD63, CD71, CD73, CD90, CD97, CD98, CD99, CD105, CD106, CD112, CD146, CD155, CD166, CD276, and CD304. Human MSCs can be characterized by the cell-surface expression of CD29, CD44, CD73, CD90, and CD105, and the absence of cell-surface expression of hematopoietic markers CD34 and CD45. Human MSCs can also be characterized by the cell-surface expression profile of CD73$^+$, CD90$^+$, CD105$^+$, CD11a$^-$, CD19$^-$, and CD34$^-$.

Accordingly, an isolated population of MSCs for enhanced differentiation can be characterized by having a cell-surface marker expression profile of: CD54$^{low}$ or CD54$^-$, CD73$^+$, CD90$^+$, CD105$^+$, CD11a$^-$, CD19$^-$, and CD34−. In another embodiment, the isolated population of MSCs for enhanced differentiation can be characterized by having a cell-surface marker expression profile of: CD54$^{low}$ or CD54−, CD29+, CD44+, CD73+, CD90+, CD105+, CD34−, and CD45−.

The invention provides for a new sub-population of MSCs that lack or have low CD54 cell-surface expression. This sub-population of MSCs allow for enhanced or superior differentiation of MSCs into different cell-lineages and cell-types, including osteoblasts, chondrocytes, and adipocytes.

As stated previously, MSCs can be obtained from a variety of tissues. In one embodiment, MSCs are obtained from bone marrow using standard procedures known in the art. For example, bone marrow aspirates can be collected from consenting healthy donors. Human MSCs (hMSCs) can be isolated and cultured as previously described (for example, Aggarwal & Pittenger, (2005), *Human mesenchymal stem cells modulate allogeneic immune cell responses* Blood, 105: 1815-1822). Generally, mononuclear cells are isolated from bone marrow aspirates by gradient centrifugation. Mononuclear cells are then seeded into flasks containing MSC medium, such as Dulbecco's modified Eagle medium (DMEM)-low glucose supplemented with 10 mM L-glutamine and 10% fetal calf serum (FCS). hMSC cultures are then grown at 37° C. under a humidified 5% $CO_2$ atmosphere. Nonadherent cells are removed after 24 hours (h) by washing with PBS-HSA solution. The medium is changed every 4 days and after 2 weeks the cultures should be mostly confluent. hMSCs are recovered using trypsin and re-plated as passage 1 cells. Subsequently cells can be kept in culture for at least up to 8 passages and tested routinely for the presence of MSC-associated surface molecules. Under such conditions, hMSCs maintain their multilineage capacity to differentiate into osteoblasts, chondrocytes, and adipocytes.

MSCs can also be obtained from adipose tissue. An exemplary protocol is provided in the Examples below. Description relating to MSC markers, MSC cultures, MSC tissue sources and protocols for isolation therefrom, and assays assessing MSC function can also be found in U.S. application Ser. No. 12/532,512, filed Sep. 22, 2009, the content of which is hereby incorporated by reference in its entirety.

The invention also provides the use of isolated populations of CD54$^{low}$ or CD54− MSCs for purposes of immunosuppression. In one embodiment, MSCs that have a cell-surface profile comprising CD54$^{low}$ or CD54− and cell-surface CD73 expression that is at least 1.3-fold, 1.5-fold, 1.75-fold, or 2-fold higher relative to CD54+ MSCs are useful for immunosuppression applications as such cells may exert potent immunosuppressive effects on both CD4+ and CD8+ T cells. Beavis, P. A., et al.; and Zhang, B.

With respect to immunosuppression or immunomodulation, the subject is one in need of immunosuppression or immunomodulation and may be suffering from one or more conditions selected from: type 1 diabetes, graft-versus-host disease, autoimmune disease, inflammatory bowel disease, and cardiac disease. In one embodiment, the subject is suffering from a condition selected from the group consisting of graft-versus-host disease, type I diabetes, sclerosis, and lupus. In one embodiment, the subject is suffering from a condition selected from the group consisting of graft-versus-host disease after hematopoietic transplantation, type I diabetes, and multiple sclerosis. In one embodiment, the allogeneic CD54$^{low}$ or CD54− MSCs are administered in an amount sufficient to suppress the activation of CD4+ or CD8+ T-cells against transplantation, in type I diabetes, or in autoimmune disease.

Recently, MSCs have been found to be immunosuppressive against natural killer (NK) cells when grown in MLCs (mixed lymphocyte cultures) at a ratio greater than 1:10 MSC to NK cells. Additionally, MSCs have recently been found to play a significant role in dampening neutrophils' respiratory burst cycle through IL-6 secretion, which in turn preserves neutrophil lifespan in critical reserve sites such as the lungs and bone marrow. When cultured with monocytes, MSCs inhibit the differentiation of dendritic cells and further reduce their potential to activate CD4+ T-cells through the down-regulation of MHC class II molecules. Furthermore, when co-cultured with mature dendritic cells, MSCs have been found to reduce secretion of the inflammatory cytokines TNF-α, IL-12, and IFN-γ, while promoting the release of immunosuppressive IL-10. See, Reddy, et al., Mesenchymal stem cells as immunomodulator therapies for immune-mediated systemic dermatoses, Stem Cells & Dev., 2012, 21(3): p. 352-62, the content of which is incorporated by reference in its entirety. Thus, in some embodiments, the CD54$^{low}$ or CD54− MSCs described herein are immunosuppressive against the activation and/or function of natural killer cells, neutrophils, T cells, dendritic cells, and/or B-cells. These immunomodulatory properties of the CD54$^{low}$ or CD54− MSCs described herein may be used as therapeutic treatment for graft-versus-host disease after hematopoietic transplantation, type I diabetes, and multiple sclerosis. In one embodiment, CD54$^{low}$ or CD54− MSCs cells described herein may be used in the induction and maintenance of immune system regulation in post-infectious, inflammatory, allergic, autoimmune, allo-immune, vasculitic, degenerative vascular, and graft-versus-host diseases.

EXAMPLES

Isolation and Cultivation of AMSCs

AMSCs were isolated from lipoaspirate using a modified method as described [23]. Briefly, lipoaspirate was obtained and washed with equal volume of hank's buffered salt solution (HBSS; Invitrogen, Grand Island, NY). After gentle shaking, isolated samples were separated into two phases. The lower phase (containing stem cells, adipocytes, and blood) was washed and enzymatically dissociated with 0.075% collagenase type I (Sigma-Aldrich, St. Louis, MO)/HBSS for 1 h at 37° C. with gentle shaking. Collagenase was inactivated by adding a 1:10 volume of fetal bovine serum (FBS) to adipose collagenase mixture.

The mixture was centrifuged at 400 g for 10 min at 25° C. The cellular pellet was resuspended in red blood cell lysis buffer (eBioscience, San Diego, CA) and incubated at 25° C. for 10 min. The pellet was resuspended in washing medium (HBSS with 2.4% FBS) and sequentially passed through 100, 70, and 40 μm mesh filters to remove cell masses. An equal amount of HISTOPAQUE-1077 (Sigma-Aldrich) was added and centrifuged at 400 g for 30 min to separate MSCs. Cells were seeded at $1-2 \times 10^4$ cells/cm$^3$ and grown at 37° C. in dulbecco's modified eagle medium-High Glucose (DMEM, Invitrogen) with 10% FBS and 1% penicillin/streptomycin and equilibrated against 5% $CO_2$ and 95% air.

Media was changed every 2-3 days. At 70-80% confluency, cells were washed with PBS and then detached with 0.25% trypsin-EDTA (Invitrogen). Cells were centrifuged at 300 g for 5 min. After removing the supernatant, cells were then resuspended in DMEM culture media and seeded at approximately 5×10³ cells/cm³ counting as passage one. MSCs were harvested at 70-90% confluency for RNA extraction, flow cytometry, or magnetic-activated cell sorting (MACS) at early (≤5) passage.

Human adult dermal fibroblasts (ATCC, Manassas, VA) were cultured in DMEM-high glucose (Invitrogen) with 10% FBS and 1% penicillin/streptomycin at 37° C. in an incubator with 5% $CO_2$. Cells were harvested at 70-90% confluency for mRNA extraction and flow cytometry.

Real-Time and Semi-Quantitative RT-PCR

Harvested cells were homogenized using cell shredders (Qiagen Inc, Valencia, CA). Lysates were collected and total RNA retrieved using a Qiagen RNA isolation mini kit (Qiagen Inc, Valencia, CA). RNA purity was determined using spectrophotometry at 260/280 nm. cDNA was synthesized from 2 μg of purified total RNA using reverse transcriptase (SuperScript III kit, Invitrogen).

Real-time PCR was performed using SYBR green PCR core reagents (Applied Biosystems, Foster City, CA) following the manufacturer's protocol on an ABI Fast Real Time PCR 7900 System (Applied Biosystems, Foster City, CA) as previously described. All primers (see Table 1) were designed using the Primer3 program (Whitehead Institute, Cambridge, MA). The PCR protocols involved activation of DNA polymerase followed by 40 cycles of denaturation at 94° C. for 15 s, and annealing and extension at 60° C. for 1 min. Each sample was analyzed in triplicate. Reactions without template were used as negative controls. β-actin mRNA was used as an internal control. Standard curves were plotted for each target gene and internal control. RNA quantity was expressed relative to the corresponding β-actin mRNA control. Relative expression levels were calculated using the standard curve method recommended by Applied Biosystems.

TABLE 1

The sequences of primers used in study.

| Gene | Direction | Sequence (5'->3') | Fragment Length | Gene Bank Number |
|---|---|---|---|---|
| CD54 | F | GGCTGGAGCTGTTTGAGAAC (SEQ ID NO: 1) | 249 | NM_000201 |
|  | R | TCACACTGACTGAGGCCTTG (SEQ ID NO: 2) |  |  |
| CD49d | F | GTTTTCCAGAGCCAAATCCA (SEQ ID NO: 3) | 185 | NM_000885 |
|  | R | GCCAGCCTTCCACATAACAT (SEQ ID NO: 4) |  |  |
| CD73 | F | CGCAACAATGGCACAATTAC (SEQ ID NO: 5) | 241 | NM002526 |
|  | R | CTCGACACTTGGTGCAAAGA (SEQ ID NO: 6) |  |  |
| CD81 | F | TCATCCTGTTTGCCTGTGAG (SEQ ID NO: 7) | 270 | NM_003756 |
|  | R | CCTCCTTGAAGAGGTTGCTG (SEQ ID NO: 8) |  |  |
| CD90 | F | CACACATACCGCTCCCGAACC (SEQ ID NO: 9) | 190 | NM_006288 |
|  | R | GCTGATGCCCTCACACTTGACC (SEQ ID NO: 10) |  |  |
| CD105 | F | TGCCACTGGACACAGGAT AA (SEQ ID NO: 11) | 205 | NM000188 |
|  | R | CCTTCGAGACCTGGCTAGTG (SEQ ID NO: 12) |  |  |
| CD109 | F | GTCTCCTTCCCACATCCTCA (SEQ ID NO: 13) | 192 | NM_133493 |
|  | R | CAGCTTCTTTCCCAAACTGC (SEQ ID NO: 14) |  |  |
| CD146 | F | ACCCTGAATGTCCTCGTGAC (SEQ ID NO: 15) | 202 | NM_006500 |
|  | R | TCTCTGTGGAGGTGCTGTTG (SEQ ID NO: 16) |  |  |
| CD164 | F | AAGTGGGGAACACGACAGAC (SEQ ID NO: 17) | 159 | NM_001142401 |
|  | R | TGAAACTGGCTGCATCAAAG (SEQ ID NO: 18) |  |  |

TABLE 1-continued

The sequences of primers used in study.

| Gene | Direction | Sequence (5'->3') | Fragment Length | Gene Bank Number |
|---|---|---|---|---|
| CD172a | F | TGGTAGTGCAGCCTTCTGTG (SEQ ID NO: 19) | 101 | NM-080792 |
|  | R | GGCATTGGGTCTCGATAAGA (SEQ ID NO: 20) |  |  |

Semi-quantitative PCR was performed in a Bio-Rad DNA Engine thermal cycler using the appropriate oligonucleotide primer pairs (see Table 1). 15 µL of each PCR product was detected by ethidium bromide gel electrophoresis using a 1% agarose gel. Each sample was tested in triplicate. Data were analyzed using Alpha Innotech's AlphaEase® FC Software: FluorChem HD2 version 6.0.2. Intensities were measured using the spot-denso tool. The relative expression level was taken as a ratio over the expression of the house keeping gene β-actin.

Flow Cytometry $1 \times 10^5$ cells were collected, washed, blocked with 10% goat serum (Abcam, Cambridge, MA) and diluted in PBS containing 3% BSA (Sigma-Aldrich) for 20 min at 4° C. Cells were then incubated with 2 µg/mL of CD54 antibody (Biolegend, San Diego, Calif,) for 1 h at 4° C. Isotype-matched control antibody was used at the same concentration as the primary antibody to evaluate non-specific binding. After 3 washes with PBS, cells were incubated with FITC-conjugated goat anti-mouse secondary antibody for 30 min in the dark at 4° C. followed by 3 washes with PBS. Cells were resuspended in PBS containing 3% BSA. Propidium iodide (Vector laboratories, Burlingame, CA) was added at a final concentration of 0.02 µM for live cell gating. Ten-thousand events were acquired with a FACScaliber flow cytometer (Becton Dickenson, Mountain View, CA) and results were analyzed with CellQuest software program (Becton Dickenson). The cutoff level defined by the isotype control antibody was set to less than 1%. The mean fluorescent intensity (MFI) ratio was calculated by dividing the MFI of CD54 antibody by the MFI of the isotype control antibody.

Magnetic-Activated Cell Sorting

MACS was performed according to protocols described by Milenyi Biotech Inc (Auburn, CA). Briefly, $1 \times 10^6$ cells were labeled with 2 µg anti-CD54 antibodies in 100 µL PBS, incubated for 1 h at 4° C. and then washed with PBS. Cells were centrifuged at 300 g for 10 min. The supernatant was aspirated and cells were resuspended in 50 µL of MACS buffer. 20 µL of goat anti-mouse IgG1 conjugated microbeads were added to cells and incubated at 4° C. for 30 min. Cells were then washed, collected, and resuspended in 500 µL of buffer. MACS columns attached to the magnetic sorter were first rinsed with 3 mL of buffer and eluent discarded. Cells were then applied to the columns and washed with 3 mL of buffer 3 times, and eluent collected in a single centrifuge tube labeled as CD54⁻ cells. Columns were then removed from the magnetic sorter and 5 mL of buffer was immediately applied. The eluent was collected in a fresh centrifuge tube and labeled as CD54⁺ cells.

Sorted cells were cultured in a 6 well plate with 2 mL of DMEM-High Glucose (Invitrogen) with 10% FBS and 1% penicillin/streptomycin. Cells were allowed 1 day to recover before they were harvested for mRNA or subjected to either adipogenic or osteogenic differentiation.

CFU-F Assay

Various adipose-derived MSC (AMSC) lines (sorted and unsorted) were seeded at 156 cells/cm³ on 6 well plates in triplicate, cultured for 14 days, and then stained with 0.5% crystal violet (Sigma-Aldrich) in 25% methanol to evaluate clone number.

MSC Differentiation

Reagents used in adipogenic and osteogenic differentiation assays were purchased from Sigma-Aldrich unless otherwise indicated. AMSCs used in the adipogenesis assay were seeded at $1.5 \times 10^4$ cells/cm³. Adipogenic induction medium was comprised of DMEM with 4.5 g/L glucose, 2 mM glutamine, 10% FBS, 1% penicillin/streptomycin (Invitrogen) containing 0.5 M IBMX, $2.5 \times 10^{-3}$ M dexamethasone, 1.7 mM insulin, and 140 mM indomethacin. Adipogenic induction medium was applied 1 day after seeding and replaced every 3 days thereafter. Cells were stained with oil red O at 14 days.

AMSCs used in the osteogenesis assay were seeded at $2.5 \times 10^3$ cells/cm³. Osteogenic induction medium was comprised of DMEM with 4.5 g/L glucose, 2 mM glutamine, 10% FBS, 1% penicillin/streptomycin (Invitrogen) containing 1 M beta-glycerophosphate, $2.5 \times 10^{-3}$ M dexamethasone, and 10 mg/mL ascorbic acid. Osteogenic induction medium was applied 1 day after seeding and replaced every 3 days thereafter. Cells were stained with alazirin red S at 21st day.

Statistical Analysis of Data

All data are expressed as means±standard error of the mean (SEM) of 3 independent experiments. Analysis of significance was performed using a 2-tailed student t-test with $p<0.05$ considered significant.

Expression of CD54 Marker in AMSCs and Fibroblasts

In vitro expanded human AMSCs displayed typical morphology. RT-PCR data demonstrated AMSCs were positive for expression of CD73, CD90, and CD105, and negative for expression of CD11a, CD19, CD34, CD45, and HLA-DR (data not shown). As shown in FIG. 1, AMSCs and primary human dermal fibroblasts were harvested and total RNA was isolated. Real-time RT-PCR was conducted to examine the expression of CD49d, CD54, CD81, CDD109, CD146, CD164, and CD172a. Y-axis refers to expression levels normalized to β-actin. *p<0.05. FIG. 1 shows there was no statistical difference in the relative expression levels of CD81, CD109, CD146, CD164, and CD172a in AMSCs versus fibroblasts whereas fibroblasts expressed significantly higher CD49d and 10.3-fold greater levels of CD54. Thus, CD54 was selected for further analysis.

Figure 2:
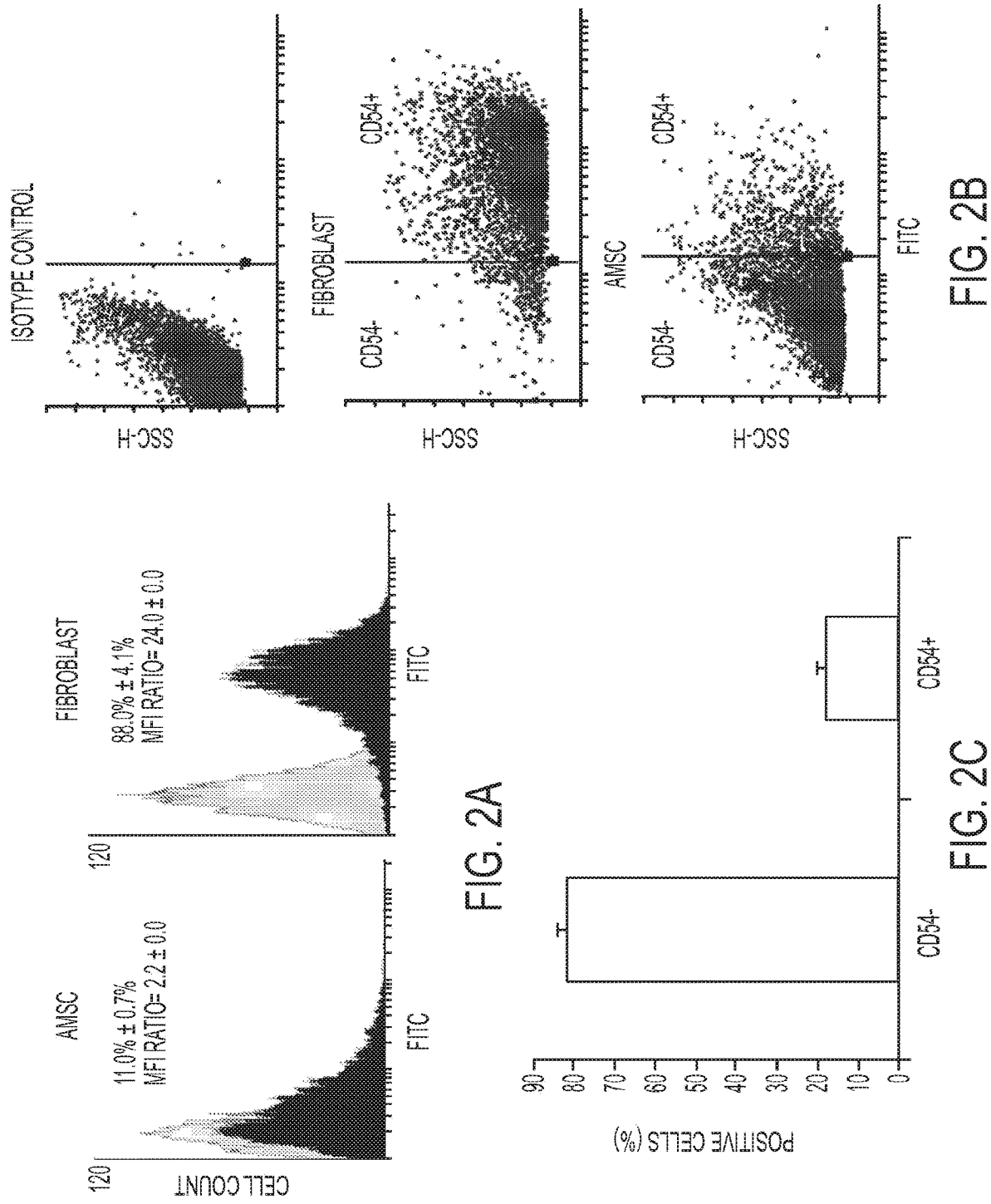
FIG. 2A-2C. Quantitative evaluation of CD54 protein expression in AMSCs and fibroblasts. (A) Early passage AMSCs and primary human dermal fibroblasts were stained with anti-CD54 specific antibody (black histograms) or an isotype-matched control antibody (grey histograms). (B) Cells stained with anti-CD54 specific antibody or an isotype-matched control antibody was gated on side scatter dot plot versus the FITC profile. (C) Early passage AMSCs were harvested and sorted with anti-CD54 specific antibody by MACS.

Flow cytometry data illustrated that 88.0%±4.1% fibroblasts strongly express CD54 on the cell surface with a MFI ratio of 24.0±0.0 while only 11.0%±0.7% of AMSCs showed weak staining (FIG. 2, (A) & (B)). As shown in FIG.

2(B), expression of CD54 was analyzed by flow cytometry. MFI of CD54 reactivity normalized to the MFI of the isotype control. Means±SEM for 3 independent runs are shown. MACS was used to sort the expanded AMSCs at early passage with anti-CD54 antibody. Consequently two new subpopulations, CD54⁻ and CD54⁺ AMSCs were created. It was found that 15.8%±1.9% of AMSCs were CD54⁺ (FIG. 2(C)).

Phenotypic and CFU Analysis of CD54⁻ and CD54⁺ AMCS

Figure 3:
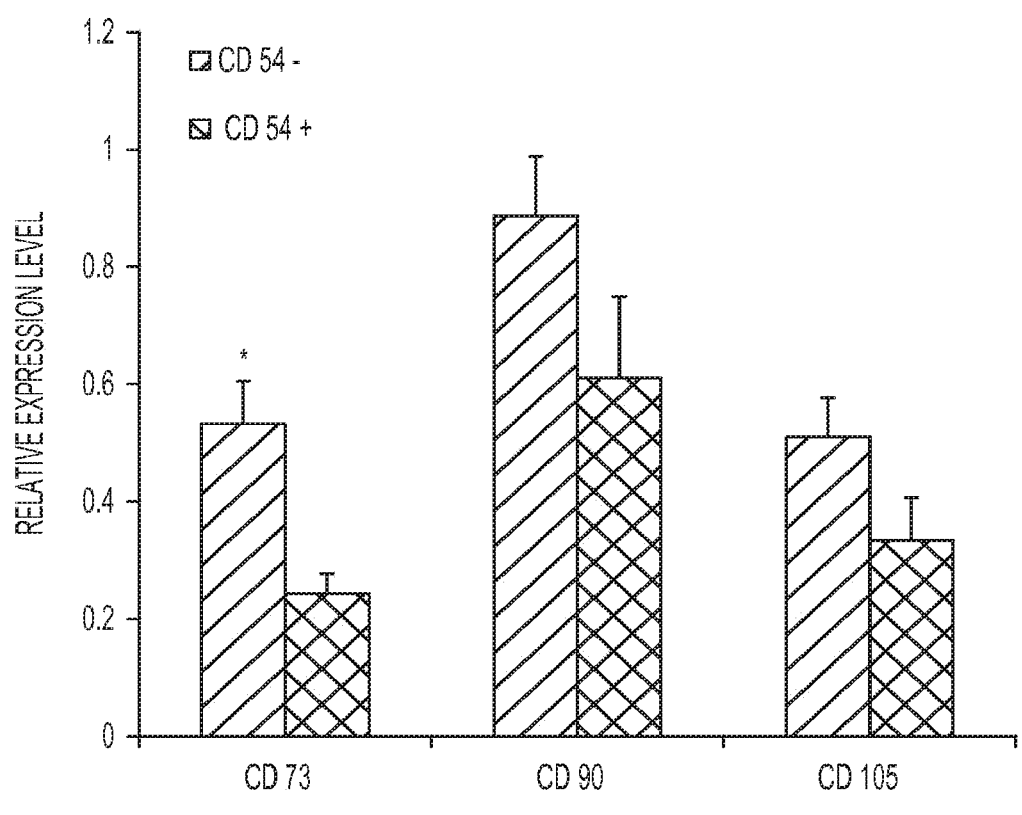
FIG. 3. Expression of standard MSC markers in CD54$^-$ and CD54$^+$ AMSC populations. Semi-quantitative PCR was performed using primers specific for CD73, CD90 and CD105.

RNA was isolated from CD54⁻ and CD54⁺ AMSC fractions and analyzed for expression of MSC markers using semi-quantitative RT-PCR. Fifteen μL of each PCR product was detected by ethidium bromide gel electrophoresis using a 1% agarose gel. The relative expression level was taken as a ratio over the expression of the house keeping gene β-actin (FIG. 3). FIG. 3 demonstrates that CD73 mRNA expression was 2.2-fold higher in CD54⁻ versus CD54⁺ cells. Both fractions expressed similar levels of CD90 and CD105.

Figure 4A:
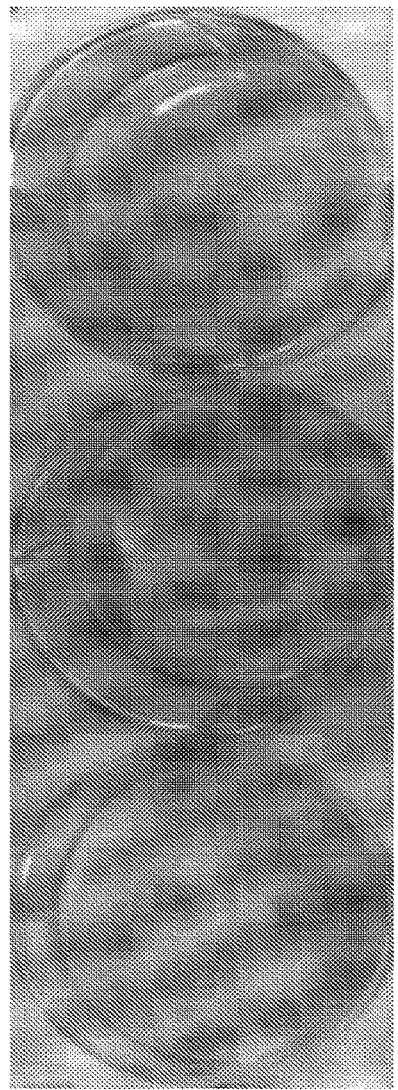
FIG. 4A-4B. Colony forming capability of CD54 sorted and unsorted AMSC populations. (A) Cells from unsorted, CD54$^-$, and CD54$^+$ fractions were seeded at 156 cells/cm$^3$ on 6-well plates in triplicate and cultured for 14 days, then stained with 0.5% crystal violet in 25% methanol. (B) Clone number was counted under light microscopy (*p<0.05).
Figure 4B:
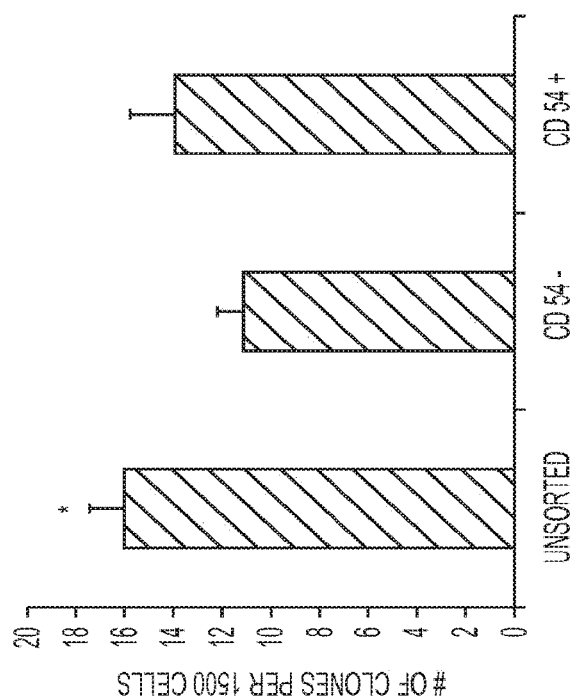

Clonogenic assays revealed that early passage unsorted AMSCs displayed the highest colony forming capability with 16 colonies per 1,500 cells seeded (FIG. 4) whereas CD54⁺ and CD54⁻ AMSCs produced 14 and 11 colonies per 1,500 cells seeded, respectively.

Adipogenic and Osteogenic Differentiation Potential of CD54⁻ and CD54⁺ AMSCs

Figure 5:
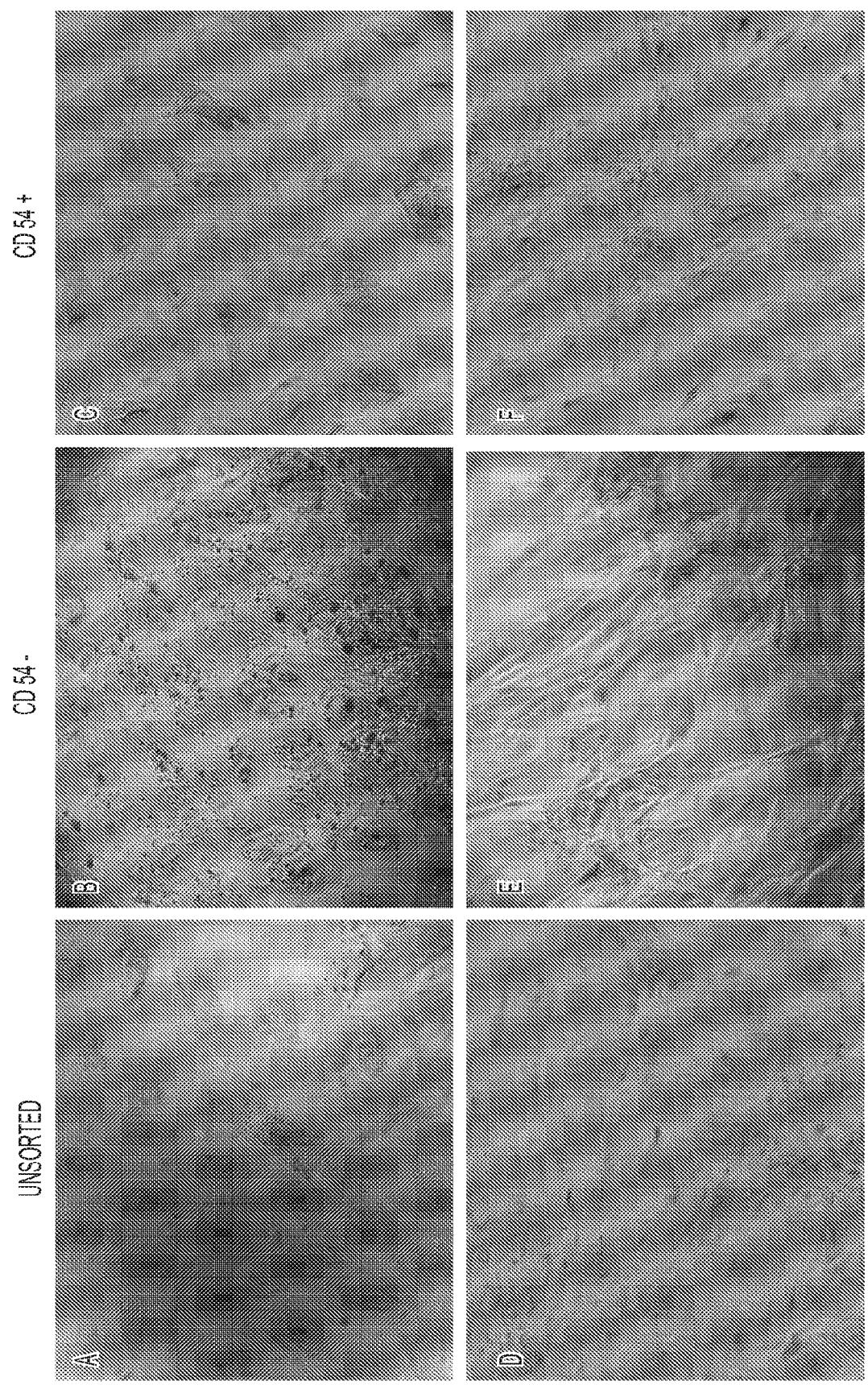
FIG. 5. Adipogenic differentiation of CD54$^-$, CD54$^+$, and unsorted AMSCs. Unsorted (A and D), CD 54$^-$ (B and E), and CD54$^+$ (C and F) AMSCs were cultured in adipogenic induction medium (A, B, and C) or normal DMEM medium (D, E, and F), wherein after 14 days, oil red O staining was used to illustrate intracellular lipid droplets.
Figure 6:
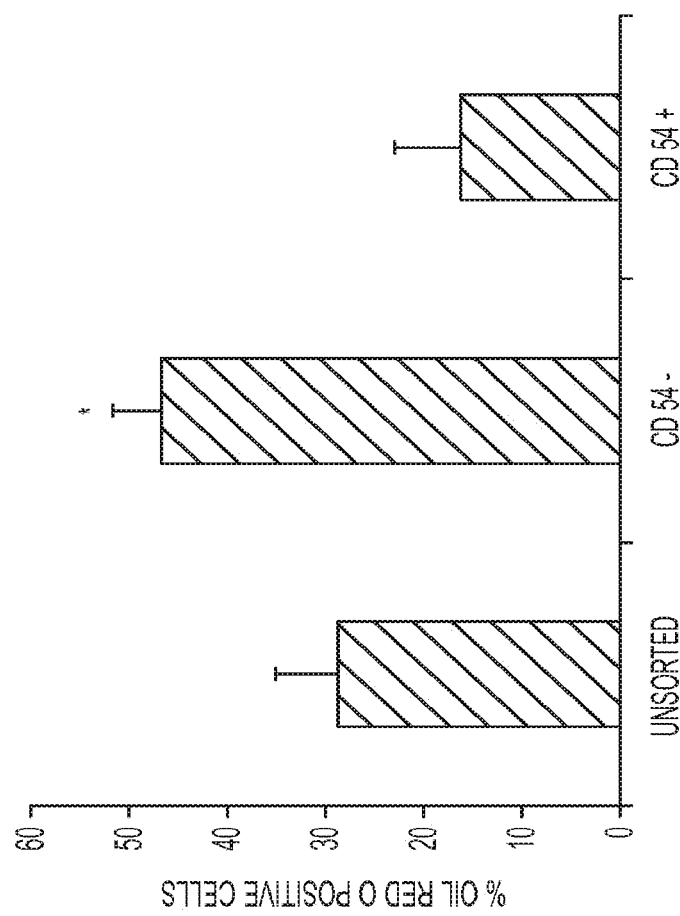
FIG. 6. Quantitative evaluation of adipogenic differentiation of CD54$^-$, CD54$^+$, and unsorted AMSCs.

After 14 days of adipogenic induction, differentiated adipocytes displayed a round shape with the formation of lipid droplets that accumulated the oil red O stain (FIG. 5 A-C). Control cells were negative for oil red O staining (FIG. 5. D-F). CD 54⁻ AMSCs showed the highest accumulation of oil red O with 46.7%±5.0% positive staining. Histological staining of lipid droplets was analyzed under light microscopy. The percentage of oil red O stained cells was calculated as the number of oil red O positive cells divided by the total number of cells as indicated by hematoxylin nuclear staining in 3 different fields (FIG. 6). Positive staining was observed in 28.7%±6.4% of unsorted AMSCs and 16.2%±6.7% of CD54⁺ AMSCs (with *$p<0.05$) (FIG. 6).

Figure 7:
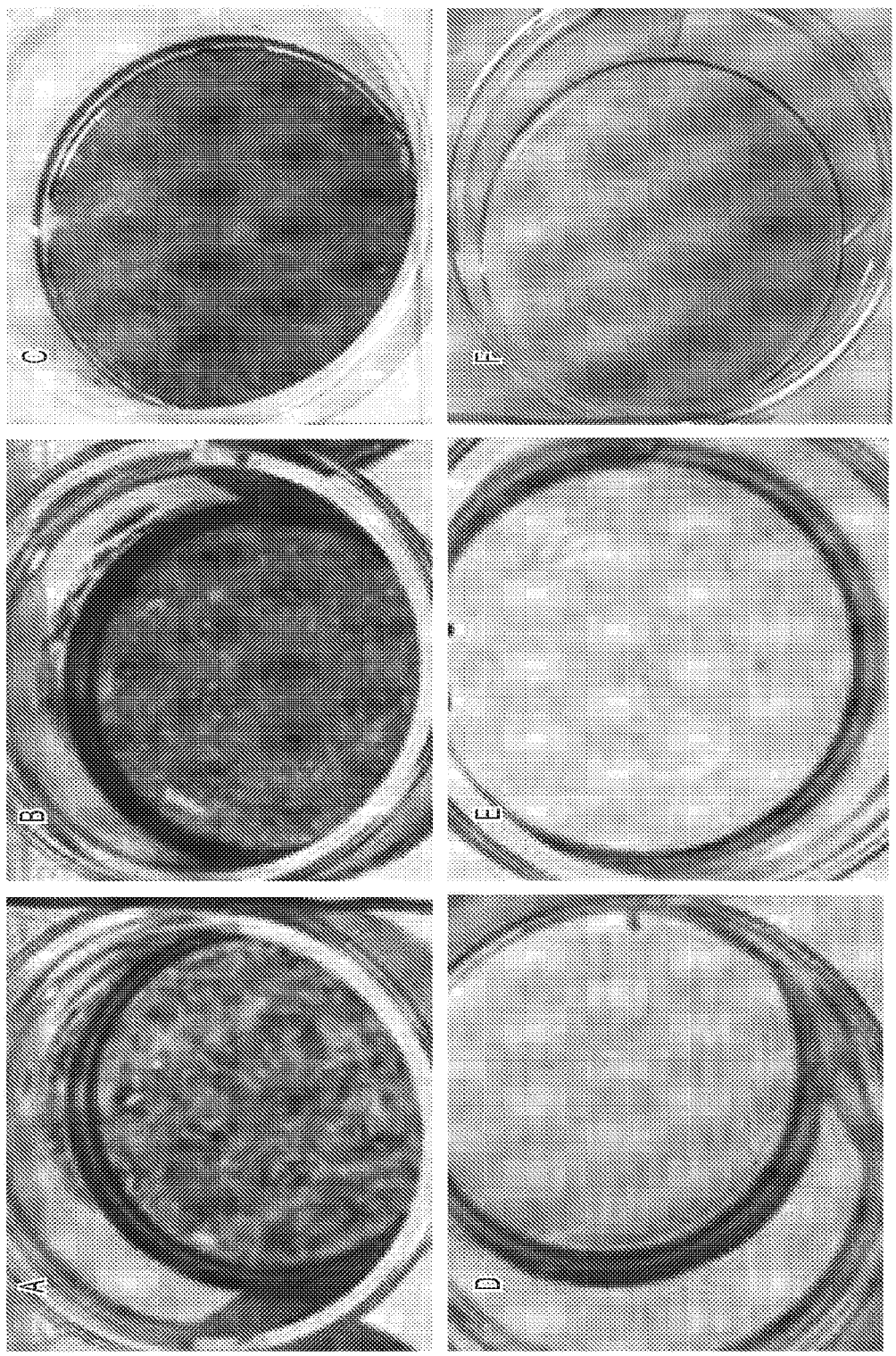
FIG. 7. Osteogenic differentiation of CD54$^-$, CD54$^+$, and unsorted AMSCs. CD 54$^+$ (A and D), CD54$^-$ (B and E), and unsorted (C and F) AMSCs were cultured in osteogenic induction medium (A, B, and C) or normal DMEM medium (D, E, and F), wherein after 21 days, alizarin red staining was used to illustrate calcification of mineralized extracellular matrix formed in the induced cells.

Osteogenic differentiation potential was assessed next. After 21 days of induction, CD54⁻ and unsorted AMSCs stained with alizarin red showed a denser extracellular matrix than did CD54⁺ cells (FIG. 7).

MSCs hold great promise in regenerative medicine but excitement has been tempered due to the possibility of fibroblast contamination. Bae, S., et al., *Combined omics analysis identifies transmembrane 4 L6 family member 1 as a surface protein marker specific to human mesenchymal stem cells*, Stem Cells Dev, 2011. 20(2): p. 197-203. Distinguishing MSCs and fibroblasts is currently not possible as both adhere to plastic and express similar levels of CD73, CD90 and CD105. This study identified a novel selection marker capable of separating MSCs from fibroblasts resulting in enhanced MSC multipotency.

CD markers were focused on because their cell surface localization allowed for their potential use in sorting procedures. Previous studies from several groups reported qualitative differences in expression of CD49d, CD54, CD81, CD109, CD146, CD164, and CD172a by MSCs and fibroblasts (Wagner, W., et al.; Covas, D. T., et al.; Pilling, D., et al., *Identification of markers that distinguish monocyte-derived fibrocytes from monocytes, macrophages, and fibroblasts*, PLoS One, 2009. 4(10): p. e7475; Lai, R. C., et al., *Exosome secreted by MSC reduces myocardial ischemia/reperfusion injury*, Stem Cell Res, 2010. 4(3): p. 214-22; Battula, V. L., et al., *Prospective isolation and characterization of mesenchymal stem cells from human placenta using a frizzled-9-specific monoclonal antibody*, Differentiation, 2008. 76(4): p. 326-36), but none of these studies confirmed their utility as selection markers. In the present study, mRNA expression levels of these CD markers were further analyzed and validated by real-time PCR, a more quantitative method. It was found that dermal fibroblasts express 10-fold more CD54 mRNA and 5-fold more CD54 cell surface protein than AMSCs. To our knowledge, this is the first quantitative comparison of CD54 mRNA and protein expression in MSCs and fibroblasts. This finding is in line with a previous report that 70-100% of human adult fibroblasts positively stained with anti-CD54 antibody using flow cytometry. Covas, D. T., et al. However, a recent study showed that only 25% of human adult dermal fibroblasts were CD54⁺, in line with AMSCs. Blasi, A., et al., *Dermal fibroblasts display similar phenotypic and differentiation capacity to fat-derived mesenchymal stem cells, but differ in anti-inflammatory and angiogenic potential*, Vasc Cell, 2011. 3(1): p. 5. This discrepancy may be explained by the difference in the experimental design, because endothelial growth medium supplemented with 10% FCS and bFGF was used to culture dermal fibroblasts (Blasi, A., et al.), whereas in our study we used DMEM supplemented with 10% FBS.

CD54, also called inter-cellular adhesion molecule 1, is a transmembrane glycoprotein with 5 extracellular immunoglobulin G-like domains and a short cytoplasmic tail that associates with multiple cytoskeletal linker proteins. Yang, L., et al., *ICAM-1 regulates neutrophil adhesion and transcellular migration of TNF-alpha-activated vascular endothelium under flow*, Blood, 2005. 106(2): p. 584-92. CD54 is primarily expressed in endothelial cells and its interaction with lymphocyte function-associated antigen-1 and macrophage antigen-1 is important for leukocyte adhesion and transendothelial migration. Yang, L., et al. It was reported that lymphocyte function-associated antigen-1-dependent monocyte migration across connective tissue barriers was primarily via engagement of CD54 on fibroblasts. Shang, X. Z. and A. C. Issekutz, *Contribution of CD11a/CD18, CD11b/CD18, ICAM-1 (CD54) and -2 (CD102) to human monocyte migration through endothelium and connective tissue fibroblast barriers*, Eur J Immunol, 1998. 28(6): p. 1970-9.

Without being bound by hypothesis, the difference in CD54 expression by MSCs and fibroblasts suggested that if MSCs became gradually overgrown by contaminating fibroblasts, expression of CD54 would increase at later passage numbers. To test this hypothesis, CD54 mRNA expression in AMSC cultures of passage 2 and 20 were compared. The results confirmed the hypothesis as CD54 expression was substantially increased in AMSCs at passage 20 (data not shown). AMSCs with anti-CD54 antibody were sorted before cell expansion to generate CD54⁺ and CD54⁻ populations. The CD73 expression was 2.2-fold higher in CD54⁻ cells relative to CD54⁺ cells, while, expression of CD90 and CD105 was similar. CD73, a membrane-bound nucleotidase, is pivotal in the conversion of immunostimulatory ATP into adenosine, which exerts potent immunosuppressive effects on both CD4⁺ and CD8⁺ T cells. Beavis, P. A., et al.; Zhang, B. Thus, increased CD73 expression in CD54⁻ AMSCs would benefit their immunosuppressive effects.

Due to the similarities in morphology and cell surface marker expression, distinction between MSCs and fibroblasts could be based on their differentiation potential. The adipogenic and osteogenic differentiation potential of CD54 sorted and unsorted AMSCs were studied and it was found that differentiation capacity was enhanced in CD54⁻ AMSCs relative to CD54⁺ cells. This data suggests that CD54 may be utilized to enrich AMSCs for early osteogenic and adipogenic progenitors. Although CD54+ cells underwent adipogenic and osteogenic differentiation, the differentiation efficiency was extremely low. The reason why these fibroblast-like cells possess the differentiation capabilities remains unknown. Recently, several papers revealed that fibroblasts derived from skin and/or other sources could be treated to differentiate into several cell types, including osteoblast and adipocyte. Lorenz, K., et al.; Blasi, A., et al.; Hee, C. K., M. A. Jonikas, and S. B. Nicoll, *Influence of three-dimensional scaffold on the expression of osteogenic differentiation markers by human dermal fibroblasts*, Biomaterials, 2006. 27(6): p. 875-84; Sommar, P., et al., *Engineering three-dimensional cartilage- and bone-like tissues using human dermal fibroblasts and macroporous gelatine microcarriers*, J Plast Reconstr Aesthet Surg, 2010. 63(6): p. 1036-46 and Junker, J. P., et al., *Adipogenic, chondrogenic and osteogenic differentiation of clonally derived human dermal fibroblasts*, Cells Tissues Organs, 2010. 191(2): p. 105-18. Our clonogenic assays illustrated CD54− AMSCs formed slightly less colonies than other populations. Without being bound by hypothesis, this may be due to the fact that the growth rate of fibroblasts (48 h per subculture) is higher than AMSCs (72 h per subculture) under our culture conditions (data not shown). It is also possible that the higher seeding density is disadvantageous in MSC expansion. Such phenomenon was already described. Niarchos, D. K., S. A. Perez, and M. Papamichail, *Characterization of a novel cell penetrating peptide derived from Bag-1 protein*. Peptides, 2006. 27(11): p. 2661-9; Colter, D. C., et al., *Rapid expansion of recycling stem cells in cultures of plastic-adherent cells from human bone marrow*, Proc Natl Acad Sci USA, 2000. 97(7): p. 3213-8.

The studies demonstrated that dermal fibroblasts express 10-fold more CD54 mRNA and 5-fold more CD54 protein on their surface than AMSCs. Cultured CD54− AMSCs expressed higher levels of CD73, an immunosuppressive molecule, and increased differentiation capacity into adipocytes and osteoblasts. CD54 was identified as a novel selection marker for distinguishing MSCs from fibroblasts. CD54 may allow for enrichment of MSCs with enhanced multipotency and immunosuppressive properties, both advantageous features for therapeutic applications.

Those skilled in the art would readily appreciate that all parameters and examples described herein are meant to be exemplary and that actual parameters and examples will depend upon the specific application for which the composition and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. Accordingly, those skilled in the art would recognize that the use of a composition or method in the examples should not be limited as such. The present invention is directed to each individual composition, or method described herein. In addition, any combination of two or more such compositions or methods, if such composition or methods are not mutually inconsistent, is included within the scope of the present invention.

What is claimed is:

1. A method of cell transplantation into a human recipient, the method comprising:
    isolating a population of mammalian mesenchymal stem cells (MSCs) by a method comprising:
        obtaining and processing adipose tissue or bone marrow by enzymatic dissociation using collagenase type 1 to release MSCs from the tissue, followed by inactivation of collagenase with fetal bovine serum (FBS) to form a sample;
        centrifuging the sample to form a cellular pellet;
        resuspending the pellet in red blood cell lysis buffer to lyse red blood cells, followed by sequential filtering through mesh filters to remove large cell masses and debris;
        enriching the MSC population through density gradient centrifugation to further separate MSCs from other cell types;
        culturing the MSCs in Dulbecco's Modified Eagle Medium (DMEM) supplemented with fetal bovine serum (FBS) and penicillin/streptomycin with CO2 until the cells reach 70-80% confluency;
        selecting the MSC population based on low or absent CD54 expression using flow cytometry or magnetic-activated cell sorting (MACS) techniques to isolate a population with a specific surface marker profile by harvesting the MSCs at early passage;
    administering the population of mammalian mesenchymal stem cells (MSCs) to a human recipient;
    wherein the population of MSCs has a cell surface expression profile comprising low cell surface expression of CD54 ($CD54^{low}$) or no cell-surface expression of CD54 ($CD54^-$), $CD73^+$, $CD90^+$, $CD105^+$, $CD11a^-$, $CD19^-$, $CD34^-$; and $CD45^-$;
    wherein the population of MSCs was selected on the basis of CD54 cell surface expression;
    wherein the population of MSCs is allogeneic with respect to the human recipient, and wherein said administering results in immunosuppression in said human recipient.

2. The method of claim 1, wherein the population of MSCs comprises greater than 50% of $CD54^{low}$ or $CD54^-$ MSCs.

3. The method of claim 1, wherein the MSCs comprises less than 5% of contaminating fibroblasts.

4. The method of claim 1, wherein the MSCs is adipose-derived MSCs or bone-marrow derived MSCs.

5. The method of claim 1, wherein the MSCs expresses cell-surface CD73 at a level at least 1.25-fold greater than allogeneic $CD54^+$ MSCs or MSCs that are unsorted or unseparated on the basis of cell-surface CD54 expression.

6. The method of claim 1, wherein the administering is done by injecting the isolated population into a human recipient.

7. The method of claim 1, wherein the MSCs has enhanced MSC differentiation potential in comparison to $CD54^+$ MSCs or MSCs that are not selected on the basis of cell-surface CD54 expression.

8. The method of claim 1, wherein the MSCs are rodent, bovine, equine, primate, or human MSCs.

9. The method of claim 1, wherein the population of MSCs further express at least one cell-surface marker chosen from the group consisting of HLA-G, HLA-E, indoleamine-pyrrole 2,3, dioxygenase (INDO), and CD200.

10. The method of claim 1, wherein the human recipient suffers from diabetes, a graft-versus-host disease, an autoimmune disease, an inflammatory disease a cardiac disease, an allo-immune disease, an allergic disease or a degenerative vascular disease.

11. The method of claim 10, wherein the human recipient suffers from type 1 diabetes.

12. The method of claim 1, wherein the human recipient suffers from multiple sclerosis.

13. The method of claim 1, wherein the human recipient suffers from lupus.

14. The method of claim 1, wherein the population of MSCs selected on the basis of CD54 cell surface expression was sorted using an anti-CD54 antibody.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggctggagct gtttgagaac                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcacactgac tgaggccttg                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```
gttttccaga gccaaatcca                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gccagccttc cacataacat                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcaacaatg gcacaattac                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcgacactt ggtgcaaaga                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcatcctgtt tgcctgtgag                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctccttgaa gaggttgctg                                              20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacacatacc gctcccgaac c                                            21

```
<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgatgccc tcacacttga cc                                              22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgccactgga cacaggataa                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccttcgagac ctggctagtg                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtctccttcc cacatcctca                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagcttcttt cccaaactgc                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
accctgaatg tcctcgtgac                                                 20
```

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tctctgtgga ggtgctgttg					20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
aagtggggaa cacgacagac					20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tgaaactggc tgcatcaaag					20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tggtagtgca gccttctgtg					20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ggcattgggt ctcgataaga					20